United States Patent [19]

Montanari

[11] 3,960,882

[45] June 1, 1976

[54] CHEMICAL COMPOUNDS FOR TRICHOMONIASIS AND CANDIDIOSIS TREATMENT

[76] Inventor: Roberto Montanari, Viale Bianca Maria 2, 20122 Milan, Italy

[22] Filed: Feb. 10, 1975

[21] Appl. No.: 548,739

[30] Foreign Application Priority Data

Mar. 4, 1974 Italy .................................. 48930/74
Nov. 19, 1974 Italy .................................. 29577/74

[52] U.S. Cl. ................................ 424/273; 260/309
[51] Int. Cl.² ...................................... C07D 233/94
[58] Field of Search ...................... 260/309; 424/273

[56] References Cited
UNITED STATES PATENTS 3,702,330  11/1972  Hoff et al. ........................... 260/309

OTHER PUBLICATIONS

Knoevenagel, Berichte 1896, vol. 29, pp. 172–173.
Marvel et al., J. Org. Chem. 1957, vol. 22, pp. 1451–1457.

*Primary Examiner*—Natalie Trousof
*Attorney, Agent, or Firm*—Robert E. Burns; Emmanuel J. Lobato; Bruce L. Adams

[57] ABSTRACT

Chemical compounds for Trichomoniasis and Candidiosis treatment, having chemical denomination:
ethyl ester of 3-(5-nitro-2-imidazolyl)-2-acetylpropenoic acid;
or:
ethyl ester of 3-(1-methyl-5-nitro-2-imidazolyl)-2-acetylpropenoic acid;
and method for preparing such compounds.

5 Claims, No Drawings

CHEMICAL COMPOUNDS FOR TRICHOMONIASIS AND CANDIDIOSIS TREATMENT

This invention relates to novel chemical compounds having both strong antiprotozoarian action and intense antimicotic action, such compounds having the following structural formula (I):

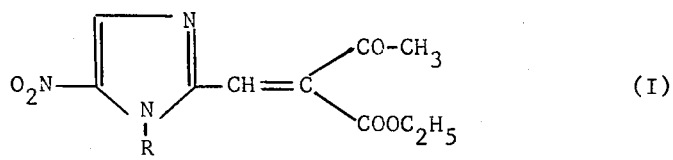

wherein R can be: —H, or —CH$_3$.

Particularly, the compounds according to the present invention exhibited a remarkable activity in treatment of *Trichomonas vaginalis* and mycetes, particularly such as *Candida Albicans*.

The present invention is also concerned with a method for preparing the compounds of the above formula (I), the method consisting of reacting 5-nitro-imidazolyl-2-carboxyaldehyde (II) with acetic acid ester (III) according to the following reaction scheme:

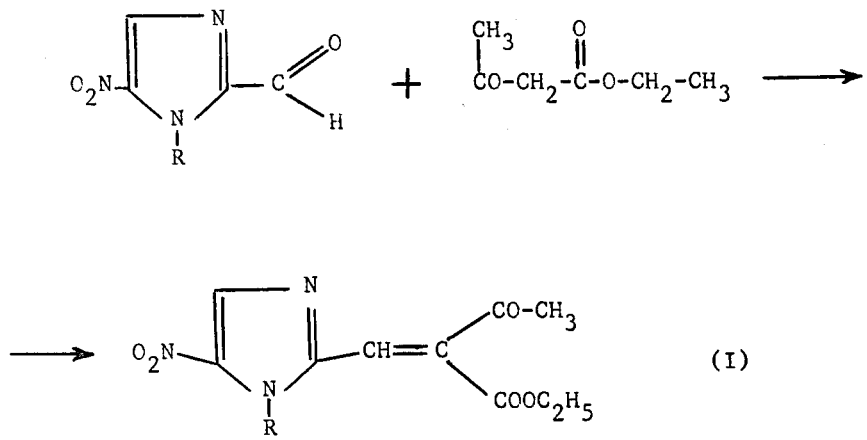

wherein: R can be: —H, or —CH$_3$.

The chemical denomination for the compounds according to the invention is respectively:

1. for R = —H:
   ethly ester of 3-(5-nitro-2-imidazolyl)-2-acetyl propenoic acid;
2. for R = —CH$_3$:
   ethyl ester of 3-(1-methyl-5-nitro-2-imidazolyl)-2-acetyl-propenoic acid.

Nitrofurane derivatives in use exhibit quite wide, but not particularly intense antibacterial spectrum, and develop Trichomonicid action thereof at substantial concentrations, so that in clinics or nursing-homes an extended dosage for more than 10 days is required for complete disappearance of infection. Such a time-extended treatment clearly evinces gastric intolerance and renal toxicity phenomena in patients.

Nitroimidazolic derivatives as presently used have not shown noteworthy antibacterial action, but show a specific trichomonicid activity of a higher intensity than that of nitrofurans. The use of these agents enables control or overcoming infection by administrating lower doses than nitrofurans, the term of treatment being however about the same. Also the use of these agents gives rise to phenomena of gastric intolerance and above all even very serious phenomena of alcohol intolerance.

In order to obviate to the above mentioned drawbacks, the present invention proposes novel imidazolic derivatives of structural formula (I), which have shown strong antiprotozoarian, antimicotic and antibacterial actions.

Antiprotozoarian activity was determined on collection stocks of Trichomonas vaginalis by minimal inhibiting concentration (M.I.C.). The results are shown in Table I, wherein the comparison molecule is metronidazol.

TABLE I

| Stocks under exam | M.I.C. (mcg/ml) | |
|---|---|---|
| | Compound of invention | Metronidazol |
| TV 70 | 0.80 | 0.70 |
| TV 70 M | 1.00 | 0.90 |
| TV 71 G | 0.90 | 0.90 |
| TV 71 A | 0.75 | 0.80 |
| TV 74 A | 0.85 | 1.00 |

Antimicotic activity was determined on stocks of Candida Albicans by minimal inhibiting concentration (M.I.C.). Methylmercadon (MMCD) was used as comparison term. The results are shown in Table II.

TABLE II

| Stocks under exam | M.I.C. (mcg/ml) | |
|---|---|---|
| | Compound of invention | MMCD |
| M$_1$ | 0.18 | 0.36 |
| M$_2$ | 0.20 | 0.48 |
| M$_3$ | 0.14 | 0.34 |

TABLE II-continued

| Stocks under exam | M.I.C. (mcg/ml) | |
| --- | --- | --- |
| | Compound of invention | MMCD |
| M₄ | 0.26 | 0.66 |
| M₅ | 0.12 | 0.34 |
| M₆ | 0.22 | 0.58 |

Antibacterial activity of the compound according to the invention is shown in Table III.

TABLE III

| Stocks under exam | M.I.C. (mcg/ml) |
| --- | --- |
| B. Cerens CICMB 43 | 1.2 |
| B. Megaterium ATCC 14581 | 3.0 |
| Str. viridans QR | 21.0 |
| St. aurens 585 | 21.5 |
| E. Coli VI | 9.5 |
| E. Coli 806 | 19.0 |
| P. Mirabilis 128 | 13.0 |
| P. Aeruginosa L | >100 |

The drug according to the invention is rapidly absorbed, and then mostly removed through renal emunctory.

Both in rat and mouse, $DL_{50}$ is 500 mg/kg by os and 350 mg/Kg by i.p. of bodily weight.

In rat and rabbit the drug is administered at a dose of 50 mg/Kg for 15 days. The animals did not suffer from such a treatment, since the behaviour thereof was always within normal limits and the major hematologic and hematochemical constants checked at the completion of 15 days treatment were also normal.

Clinical treatment is carried out orally or by topical application.

By oral treatment, 250 mg drug are administered 2–3 times a day for 3–5 days. Treatment can be extended in resistant cases.

Applications of 500 mg active element are used for local treatment.

During clinical experiment, alcohol intolerance and incompatibility phenomena were never found.

In clinic or nursing-home, 40 hospitalized patients were orally treated with a dose of 400 mg a day divided into two times. All of the patients were controlled for presence of Trichomonas. At the fifth day, no parasite was present in 39 patients, while in one patient a high attenuation of infection was found. With ambulatory patients, also partner's treatment with a same dosage was required.

The present invention can be better understood from the following preparation examples given by mere way of not limiting indication.

EXAMPLE 1

Ethyl ester of 3-(1-methyl-5-nitro-2-imidazolyl)-2-acetyl-propenoic acid 1000 ml water and 155 g (1 mole) 1-methyl-5-nitroimidazolyl-2-carboxyaldehyde of structural formula (II), wherein R = —CH₃, were introduced into a flask provided with stirrer and reflux cooler.

The solution was brought to incipient ebullition and under stirring 118 g (1 mole) acetic acid ester of structural formula (III) were added in 15 minutes. The solution was left at slight reflux for 30 minutes, then allowed to cool down at room temperature, still under stirring. The solid thus formed was filtered, vacuum dried at 50°C and crystallized from ethanol. 247 g product were obtained, m.p. 110°–111°C, with IR spectrum corresponding to the provided formula (I), with R = —CH₃. Yield was 97% on theoretical rate.

EXAMPLE 2

Ethyl ester of 3-(5-nitro-2-imidazolyl)-2-acetyl-propenoic acid.

One mole 5-nitro-imidazolyl-2-carboxyaldehyde of structural formula (II), wherein R = —H, was introduced into 500 ml glacial acetic acid, then stirring at 50°C for 5 hours. The solvent was vacuum stripped, recycled, and residue was crystallized from ethanol.

Yield was 80% product of formula (I), wherein R = —H, having analitic and IR spectrum characteristics corresponding to structure.

EXAMPLE 3

With the compound of formula (I), wherein R can indifferently be methyl radical or hydrogen, gelatinous capsules or tablets were prepared, containing 200 mg of the active compounds according to the invention.

Excipients were those as commonly used in pharmaceutical techniques or art.

EXAMPLE 4

With the compound of formula (I) according to the invention, wherein R can indifferently be methyl radical or hydrogen, powders or unguents were prepared at 2% concentration with the common formulations for local treatment.

What is claimed is:

1. A chemical compound characterized by having the following structural formula (I):

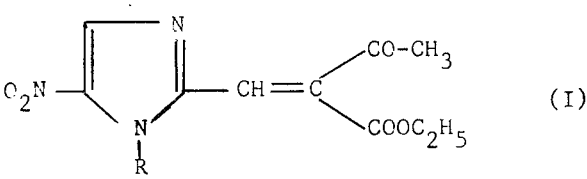

wherein R can be —CH₃ or —H.

2. The chemical compound as set forth in claim 1, the ethyl ester of 3-(5 nitro-2-imidazolyl)-2-acetyl-propenoic acid.

3. The compound as set forth in claim 1, the ethyl ester of 3-(1-methyl-5-nitro-2-imdazolyl)-2-acetyl-propenoic acid.

4. Composition for the treatment of Trichomonal and Candida Albicans infections comprising an effective amount of a compound according to claim 1 in a pharmaceutically acceptable vehicle.

5. A method for the treatment of Trichomonal and Candida Albicans infections which comprises administering orally or topically to subjects suffering from such infections an effective dosage of a composition according to claim 4.

* * * * *